United States Patent [19]

Yeh et al.

[11] Patent Number: 4,463,595
[45] Date of Patent: Aug. 7, 1984

[54] PARALLEL FLOW DIFFUSION BATTERY

[75] Inventors: Hsu-Chi Yeh; Yung-Sung Cheng, both of Albuquerque, N. Mex.

[73] Assignee: The United States of America as represented by the United States Department of Energy, Washington, D.C.

[21] Appl. No.: 466,992

[22] Filed: Feb. 16, 1983

[51] Int. Cl.³ ............................................ G01N 15/02
[52] U.S. Cl. ...................................... 73/28; 73/863.33
[58] Field of Search .................. 73/28, 863.22, 863.23, 73/863.31, 863.32, 863.33, 432 PS; 55/270

[56] References Cited

U.S. PATENT DOCUMENTS

| | | | |
|---|---|---|---|
| 3,138,029 | 6/1964 | Rich | 73/432 PS |
| 3,576,721 | 4/1971 | Mason | 73/28 |
| 3,774,442 | 11/1973 | Gustavsson | 73/28 |
| 3,983,743 | 10/1976 | Olin et al. | 73/28 |
| 4,133,202 | 1/1979 | Marple | 73/28 |
| 4,327,594 | 5/1982 | Nelson | 73/863.22 |

OTHER PUBLICATIONS

D. Sinclair et al., "Novel Form of Diffusion Battery", Am. Ind. Hyg. Ass. J., 36, pp. 39-42, Jan. 1975.
Y. S. Cheng et al., "Theory of a Screen-Type Diffusion Battery", J. Aerosol Sci., vol. 11, pp. 313-320, 1980.
Y. S. Cheng et al., "Theory and Calibration of a Screen-Type Diffusion Battery", J. Aerosol Sci., vol. 11, pp. 549-556, 1980.

Primary Examiner—Stephen A. Kreitman
Attorney, Agent, or Firm—George H. Libman; Albert Sopp; Michael F. Esposito

[57] ABSTRACT

A parallel flow diffusion battery for determining the mass distribution of an aerosol has a plurality of diffusion cells mounted in parallel to an aerosol stream, each diffusion cell including a stack of mesh wire screens of different density.

9 Claims, 3 Drawing Figures

Fig. 3

PARALLEL FLOW DIFFUSION BATTERY

BACKGROUND OF THE INVENTION

The present invention relates generally to an aerosol diffusion battery and, more particularly, to a parallel flow, screen-type diffusion battery. The U.S. Government has rights in this invention pursuant to Contract Number DE-AC04-76EV01013 between the U.S. Government and Lovelace Biomedical and Environmental Research Institute, Inc.

A diffusion battery is a useful and reliable instrument for characterizing aerosol particles of less than 0.1 micrometer ($\mu$m) in diameter. The diffusion battery directly provides the diffusion equivalent diameter (equivalent to a spherical particle with the same diffusion coefficient) of irregularly shaped particles. The conventional diffusion battery consists of several stages of diffusion cells connected serially, with each cell comprising either a collimated hole structure containing many parallel holes bundled together or a stack of wire screens. When an aerosol is passed through a diffusion cell, a portion of the aerosol diffuses to the tube wall or the wire surface and is collected there. Therefore, the aerosol concentration decreases continuously as it goes through the successive diffusion cells. By measuring aerosol concentrations at each successive stage of the diffusion battery, the fractional penetration of an aerosol can be determined. Since fractional aerosol penetration depends upon aerosol size, the size distribution from the aerosol penetration data may be estimated.

A description of one commercially available screen-type diffusion battery of the series type (Model 3040, TSI, Inc., St. Paul, Minn.) may be found in an article by the inventors entitled, "Theory of a Screen-Type Diffusion Battery", J. AEROSOL SCI., Vol. 11, pp. 313-320, 1980. This device gives an accurate reading of the particle number distribution of an aerosol. However, mathematical conversion of number distribution to mass distribution (a reading which is more useful in many toxicology studies) gives inaccurate results unless the aerosol particles are spherical.

SUMMARY OF THE INVENTION

It is an object of this invention to provide a diffusion battery which yields a direct indication of aerosol mass size distribution.

It is another object of this invention to provide a seven-cell, parallel flow, screen-type diffusion battery for the size characterization and size classification of ultra-fine aerosols.

Additional objects, advantages and novel features of the invention will become apparent to those skilled in the art upon examination of the following description or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein, the diffusion battery of this invention may comprise an intake manifold for receiving an aerosol and distributing it to a plurality of diffusion cells extending through a cell holding surface. Each cell has a tubular body extending through the surface and means for diffusing an aerosol and a filter serially mounted within the tube. The density of each diffusing means differs from the density of the diffusing means for each other cell, permitting a plurality of measurements to be simultaneously taken from each aerosol sample. In a preferred embodiment, the diffusing means comprises a number of wire screens, the number of screens being different within each cell.

BRIEF DESCRIPTION OF THE DRAWINGS

The accompanying drawings, which are incorporated in and form a part of the specification, illustrate an embodiment of the present invention and, together with the description, serve to explain the principles of the invention.

Figure 3:
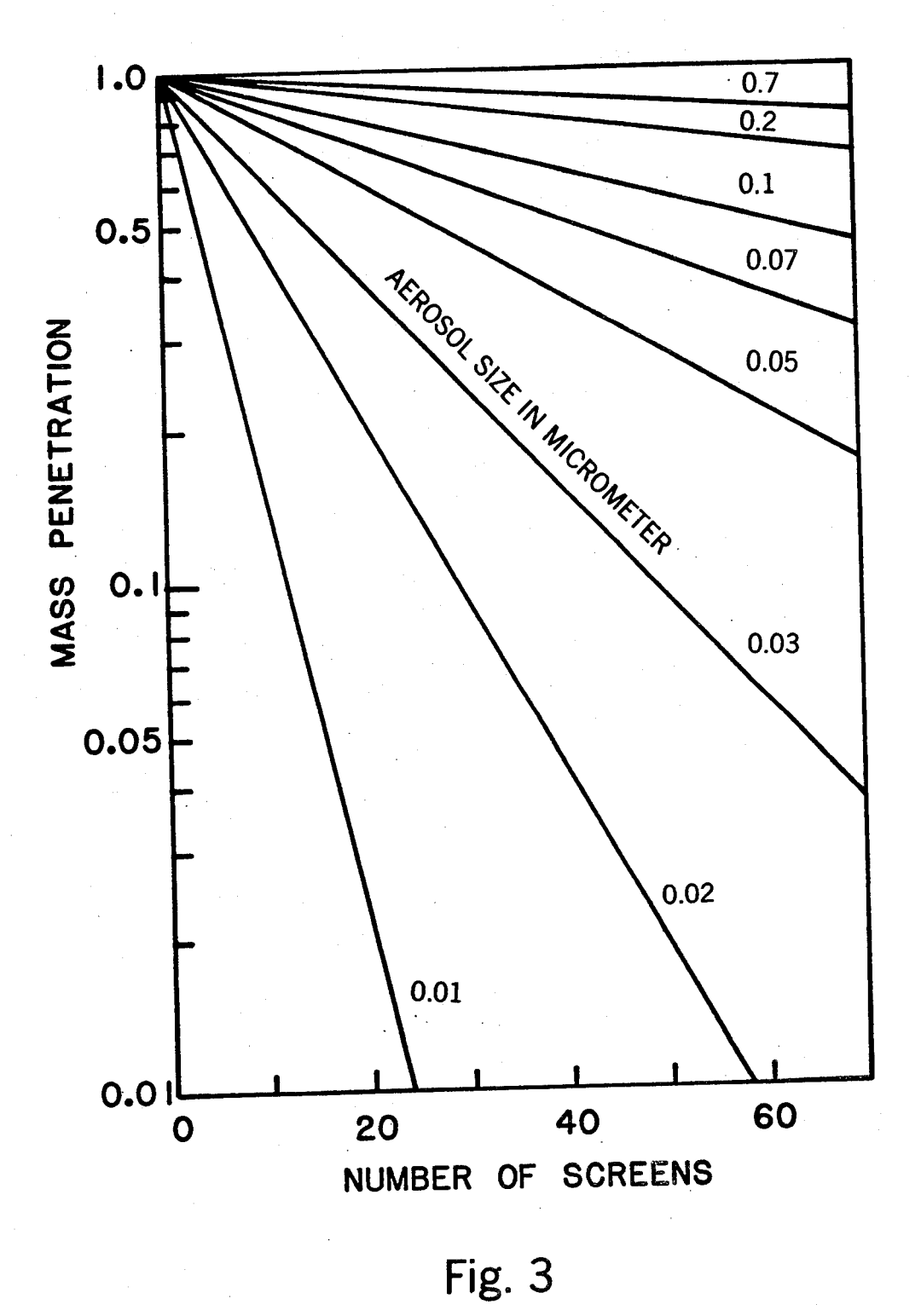

FIG. 3 is a graph showing mass penetration as a function of number of screens for a plurality of aerosol sizes.

DETAILED DESCRIPTION OF THE INVENTION

Figure 1:
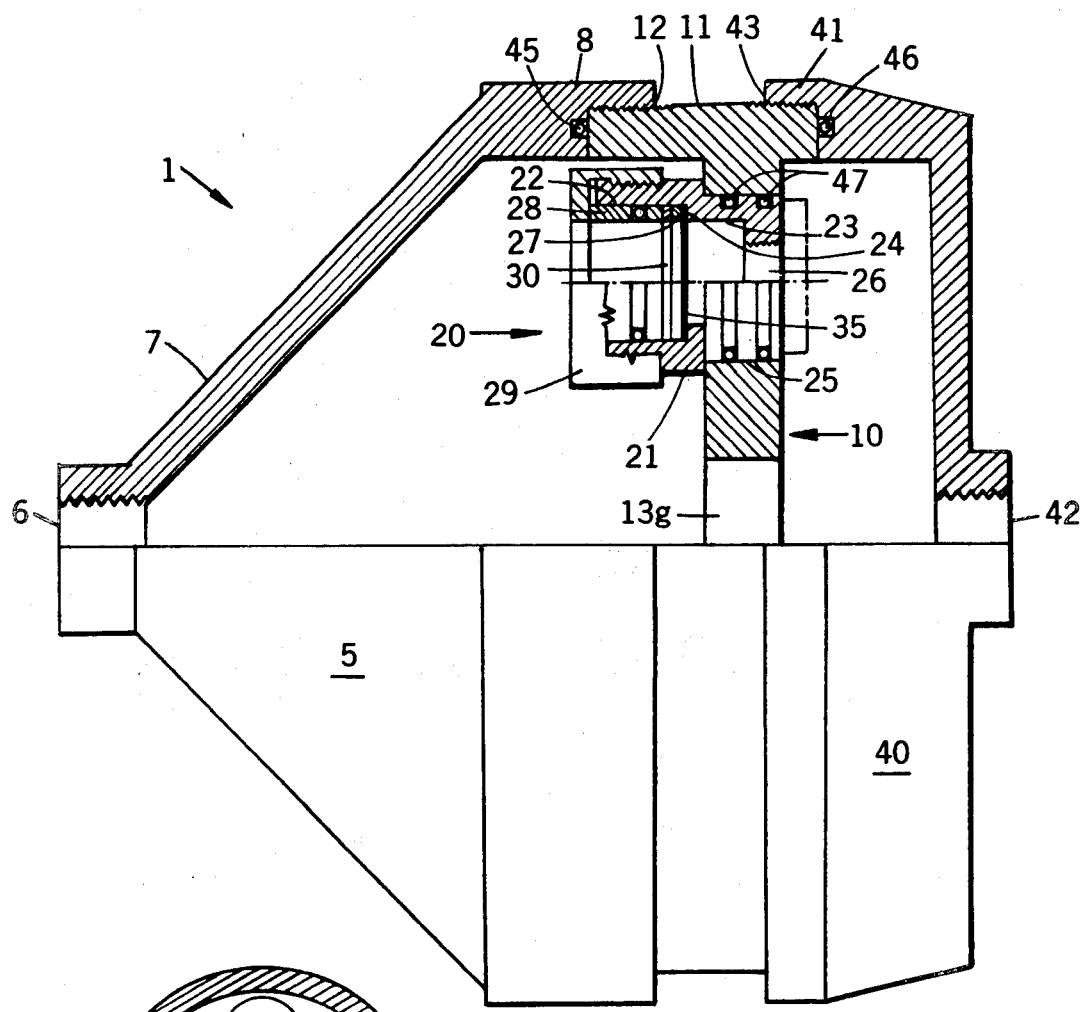
FIG. 1 is a partial cutaway of the invention, showing the detail of one diffusion cell.

FIG. 1 shows a partial cutaway view of a parallel flow diffusion battery in accordance with the preferred embodiment of this invention. Battery 1 includes an intake manifold 5, a cell holding surface 10, an output manifold 40 and a plurality of diffusion cells 20. For the sake of clarity, only one diffusion cell 20 is shown in FIG. 1. In accordance with this invention, it should be understood that there are a plurality of cells 20 located as shown and discussed hereunder in FIG. 2.

Intake manifold 5 serves as a means for distributing an aerosol evenly to each of the diffusion cells of the invention. Accordingly, intake manifold 5 includes a narrow input end 6 where the aerosol under test is fed into the device, a conical portion 7, and a wide output end 8. Intake manifold 5 may assume any configuration which ensures the even distribution of aerosol to all diffusion cells.

Cell holding surface 10 forms a support for the cells and comprises a metal plate of approximately the same area as the area of wide output end 8. Surface 10 includes an outer flange 11 extending on either side of surface 10. End 8 of intake manifold 5 fastens to flange 11 by conventional means such as screw threads 12. O-ring 45 ensures a tight seal, preventing an aerosol leak between manifold 5 and flange 11.

In a similar manner, output manifold 40 has a wide end 41 which is sealably fastened to flange 11 by means of threads 43 and O-ring 46. Output manifold 40 also includes an exhaust port 42 which may be used to safely remove the aerosol from the test environment.

Figure 2:
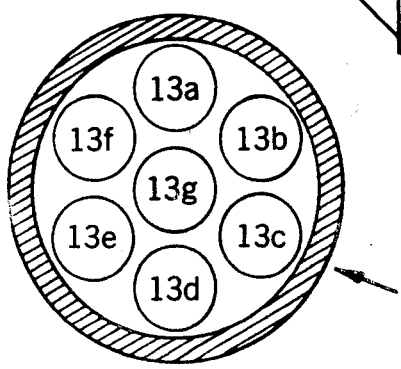
FIG. 2 is a view of the cell holding surface, showing the position of the cells within the invention.

As shown in FIG. 2, cell holding surface 10 provides a barrier between input manifold 5 and output manifold 40, except for a plurality of holes 13a–13g. Each hole is filled by one diffusion cell 20.

As shown in FIG. 1, each diffusion cell comprises a tubular body 21 having an outer surface 25 of the same outer configuration as the inner surface of hole 13, thereby permitting a tight seal between these parts. O-ring 47 ensures a tight seal between these parts. The inner surface of body 21 has a first diameter 22 over a first portion of the body extending from the input end and a second smaller diameter 23 over a second portion of body 21 extending from first portion 22. Step 24 connects the two diameters. The output end of body 21 is partially closed by a flow restricting orifice 26.

Aerosol particles are collected for measurement on a filter 35 having a diameter equal to first diameter 22 and resting against step 24. Filter 35 is retained in place by spacer 27, a ring having an outer diameter equal to first diameter 22, and an inner diameter approximately equal to second diameter 23. The side of spacer 27 opposite filter 35 forms a support for collimated hole means which, preferably, comprise a stack of wire screens 30, having an outside diameter equal to first diameter 22. Screens 30 are affixed by removable retainer spacer 28, a cylinder having the same diameters as spacer 27 and a length sufficient to extend just beyond the input end of body 21. Retainer cap 29, having a center aperture equal to second diameter 23 is threaded onto outer surface 25 of body 21 to retain filters 35 and screen 30 in a desirable position.

The principle of operation is as follows. The penetration of an aerosol through screen type diffusion battery can be described in terms of slope m as $$m = -(\log P/n) = A_0 Pe^{-\frac{2}{3}} + A_1 R^2 + A_2 Pe^{-\frac{1}{2}} R^{\frac{3}{2}}$$

where P is aerosol penetration, n is number of screens, $Pe = UD_f/D$ is the Peclet number and $R = D_p/D_f$ is the intercept parameter. $D_p$ and $D_f$ are particle diameter and screen wire diameter, respectively. U is the mean flow velocity, D is the diffusion coefficient of the particle, and $A_0$, $A_1$, $A_2$ are constants depending on the geometry and hydrodynamic parameters of the screen. FIG. 3 shows theoretical penetration curves of aerosols from 0.01 to 0.7 μm in the parallel flow diffusion battery using stainless steel 200 mesh screen and a flow rate of 1.01 liters per minute in each cell. From this theoretical equation, the aerosol size distribution is estimated by comparing the mass penetration data with the theoretical one of FIG. 3. The resultant data provides an estimate of aerosol size distribution based on mass, i.e., mass medium diameter.

In order to provide for a plurality of measurements for a single aerosol sample, each cell 20 has a screen 30 of a different density as determined by the number of screens within each cell 20. For example, holes **13*a*–13*g* may have cells 20 having 0, 10, 15, 20, 25, 30 and 35 screens respectively. Each screen of screen stack 30 can be a 200 mesh, 400 mesh or 635 mesh, and the filter 35 is 0.2 μm pore-size Zeflour filter paper. Orifice 26 of each cell 20** is sized to provide a desired flow rate of 0.55, 1 or 2 liters per minute operated under the critical condition.

The particular components and equipment discussed above are cited merely to illustrate a particular embodiment of the invention. It is contemplated that the use of this invention may involve different components as long as the principle, utilizing a number of parallel diffusion cells having regular mesh screens of differing densities, is followed. A diffusion battery so constructed will provide a sensitive, reliable measurement of the mass distribution of an aerosol. It is intended that the scope of the invention be defined by the claims appended hereto.

The procedure for a parallel flow diffusion battery measurement is as follows: First, screens 30 are cleaned and each filter 35 is weighed and recorded. The screens and filter paper are then assembled in each of diffusion cells 20 and the cells are placed within holes **13*a*–13*g* of cell holding surface 10. Intake manifold 5 and output manifold 40 are then connected and sealed. Inlet 6 is connected to an aerosol source, such as an inhalation exposure chamber or an emission source of interest. Outlet 42 is connected to a vacuum pump or a house vacuum source. After a sufficient sampling period, battery 1 is disconnected from the source and disassembled. Filter paper 35** in each cell is reweighed to determine the amount of aerosol collected or is counted for radioactivity. From this gravimetric or counting data, the aerosol penetration curve as a function of the number of screens has been determined.

The flow characteristics of a parallel flow diffusion batter constructed as shown in FIG. 1 and having an inside diameter of output manifold 40 of approximately 5 inches was checked by passing CsCl aerosol tagged with uranine into a battery having no screens. Fluorometric measurements of aerosol on the screens of each cell showed the variations of flow rate among cells to be less than 2%.

We claim:

1. A parallel flow diffusion battery for determining the mass size distribution of an aerosol, said battery comprising:

an intake manifold having input means for input of an aerosol and an output end;

a cell holding surface extending across and sealing the output end of said intake manifold; and a plurality of diffusion cells affixed to said surface, each cell comprising:

a tubular body having an inner surface and an outer surface, said outer surface extending through and sealing a hole in said holding surface;

collimated hole means for diffusing an aerosol, said means extending across and sealing the inner surface of said body; and filter means for collecting all aerosol passing through said hole structure;

the density of the hole means for each cell differing from the density of the hole means for each other cell, whereby a plurality of measurements are simultaneously taken from each aerosol sample.

2. The parallel flow diffusion battery of claim 1 wherein said intake manifold comprises a conical cap having a narrow end forming said input means and a wide end forming said output end.

3. The parallel flow diffusion battery of claim 2 wherein the outer surface of said holding surface comprises a flange extending on either side of said holding surface, said flange forming a seal with the wide end of said conical cap.

4. The parallel flow diffusion battery of claim 3 further comprising an output manifold having a wide end forming a seal with said flange and a narrow end for exhaust of said aerosol.

5. The parallel flow diffusion battery of claim 1 wherein said collimated hole means consists of a stack of wire screens, the density for each stack being varied by having a different number of screens in each stack.

6. The parallel flow diffusion battery of claim 1 including another diffusion cell having no collimated hole means, whereby said cell is used to determine a reference level.

7. The parallel flow diffusion battery of claim 5 further comprising a flow controlled critical orifice sealing the output end of said tubular body.

8. The parallel flow diffusion battery of claim 6 wherein said tubular body has an input end facing said intake manifold and an opposing output end, and said inside surface defines a circle of first diameter over a first portion of said body extending from said input end and a circle of a second, smaller, diameter over a second portion of said body extending from said first portion, said inside surface connecting said first and second portions forming a step; and said filter having an outside diameter conforming to the inside diameter of said first portion, and said filter being positioned against said step.

9. The parallel flow diffusion battery of claim 8 further including a hollow spacer ring having an outside diameter equal to said first diameter and positioned against said filter means opposite said step; wherein said collimated hole means consists of a stack of wire screens having an outside diameter equal to said first diameter, said stack being positioned against said spacer ring opposite said filter, the density for each stack being varied by having a different number of screens in each stack;

and retainer means for holding said stack against said ring.

* * * * *